United States Patent
Bronte-Stewart et al.

(10) Patent No.: US 12,109,417 B2
(45) Date of Patent: Oct. 8, 2024

(54) SYSTEMS AND METHODS FOR DEEP BRAIN STIMULATION USING KINEMATIC FEEDBACK FOR TREATMENT OF MOVEMENT DISORDERS

(71) Applicants: The Board of Trustees of the Leland Stanford Junior University, Stanford, CA (US); University of Washington, Seattle, WA (US)

(72) Inventors: Helen Bronte-Stewart, Stanford, CA (US); Yasmine Kehnemouyi, Stanford, CA (US); Matthew Petrucci, Stanford, CA (US); Jeffrey Herron, Seattle, WA (US); Johanna O'Day, Stanford, CA (US)

(73) Assignees: The Board of Trustees of the Leland Stanford Junior University, Stanford, CA (US); University of Washington, Seattle, CA (US)

( * ) Notice: Subject to any disclaimer, the term of this patent is extended or adjusted under 35 U.S.C. 154(b) by 253 days.

(21) Appl. No.: 17/649,667

(22) Filed: Feb. 1, 2022

(65) Prior Publication Data
US 2022/0241591 A1    Aug. 4, 2022

Related U.S. Application Data

(60) Provisional application No. 63/144,432, filed on Feb. 1, 2021.

(51) Int. Cl.
*A61N 1/36*    (2006.01)
*A61N 1/05*    (2006.01)

(52) U.S. Cl.
CPC ....... *A61N 1/36067* (2013.01); *A61N 1/0534* (2013.01); *A61N 1/36139* (2013.01)

(58) Field of Classification Search
CPC ............. A61B 1/36067; A61B 1/0534; A61B 1/36139; A61B 2562/0219; A61B 5/4082; A61B 5/0035
See application file for complete search history.

(56) References Cited

U.S. PATENT DOCUMENTS 8,744,587 B2    6/2014   Miesel et al.
9,943,250 B2    4/2018   Plotnik-peleg et al.
(Continued)

OTHER PUBLICATIONS

"Pathological tremor prediction using surface EMG and acceleration: potential use in "On-Off" demand driven deep brain stimulator design", Journal of Neural Engineering, vol. 10, No. 3, Jun. 2013, 36 pgs, DOI: 10.1088/1741-2560/10/3/036019.
(Continued)

*Primary Examiner* — Carl H Layno
*Assistant Examiner* — Manolis Pahakis
(74) *Attorney, Agent, or Firm* — KPPB LLP

(57) ABSTRACT

Systems and methods for deep brain stimulation using kinematic feedback in accordance with embodiments of the invention are illustrated. One embodiment includes a deep brain stimulation system, including an implantable neurostimulator, a first inertial measurement unit (IMU), a second IMU, and a controller, where the controller is communicatively coupled to the implantable neurostimulator, the first IMU, and the second IMU, and where the controller is configured to obtain kinematic data from the first IMU and the second IMU, identify an abnormal movement event based on the kinematic data, and modify deep brain stimulation provided by the implantable neurostimulator based on the identified abnormal movement event.

12 Claims, 5 Drawing Sheets

(56) References Cited

U.S. PATENT DOCUMENTS

| | | | |
|---|---|---|---|
| 10,251,595 B2* | 4/2019 | Heruth | A61M 5/1723 |
| 10,786,199 B1 | 9/2020 | Giuffrida et al. | |
| 10,786,625 B1 | 9/2020 | Giuffrida et al. | |
| 2005/0240242 A1 | 10/2005 | Dilorenzo | |
| 2007/0250134 A1* | 10/2007 | Miesel | A61N 1/36003 607/45 |
| 2007/0255118 A1* | 11/2007 | Miesel | A61N 1/36082 600/300 |
| 2009/0099627 A1* | 4/2009 | Molnar | A61N 1/36031 604/66 |
| 2009/0105785 A1* | 4/2009 | Wei | A61N 1/36132 600/301 |
| 2009/0264789 A1* | 10/2009 | Molnar | A61N 1/36135 600/595 |
| 2013/0331906 A1* | 12/2013 | Krueger | A61N 1/36067 607/45 |
| 2014/0257047 A1* | 9/2014 | Sillay | H04L 63/10 600/595 |
| 2017/0095670 A1* | 4/2017 | Ghaffari | A61N 1/36139 |
| 2017/0156663 A1 | 6/2017 | Heruth et al. | |
| 2017/0165481 A1* | 6/2017 | Menon | A61N 1/36139 |
| 2017/0258370 A1 | 9/2017 | Plotnik-peleg et al. | |
| 2018/0078770 A1* | 3/2018 | Rickert | A61B 5/4836 |
| 2018/0085572 A1 | 3/2018 | Stanslaski et al. | |
| 2018/0085585 A1 | 3/2018 | Stanslaski et al. | |
| 2018/0140842 A1* | 5/2018 | Ó Laighin | A61B 5/112 |
| 2019/0009087 A1* | 1/2019 | Çakmak | A61B 5/296 |
| 2019/0030338 A1* | 1/2019 | Wu | A61N 1/37247 |
| 2019/0151646 A1* | 5/2019 | Cakmak | A61B 5/4836 |
| 2021/0187301 A1* | 6/2021 | Paek | A61N 1/3787 |
| 2022/0062549 A1* | 3/2022 | Robison | A61B 5/251 |
| 2022/0118256 A1* | 4/2022 | Ó Laighin | A61N 1/36003 |
| 2022/0266039 A1* | 8/2022 | Giftakis | A61N 1/37247 |
| 2022/0296894 A1* | 9/2022 | Jung | A61B 5/0022 |
| 2023/0134637 A1* | 5/2023 | Brodie | A61N 1/36031 607/48 |
| 2023/0191126 A1* | 6/2023 | Kent | A61N 1/36025 607/48 |
| 2023/0271012 A1* | 8/2023 | Fischer | A61N 1/36189 607/72 |

OTHER PUBLICATIONS

Amboni et al., "Prevalence and associated features of self-reported freezing of gait in Parkinson disease: The Deep Fog study", Parkinsonism and Related Disorders, vol. 21, No. 6, Jun. 1, 2015, Electronic Publication: Apr. 13, 2015, pp. 644-649, doi: https://doi.org/10.1016/j.parkreldis.2015.03.028.

Anidi et al., "Neuromodulation targets pathological not physiological beta bursts during gait in Parkinson's disease", Neurobiology of Disease, vol. 120, Dec. 2018, pp. 107-117, doi: https://doi.org/10.1016/j.nbd.2018.09.004.

Blumenfeld et al., "Sixty-hertz stimulation improves bradykinesia and amplifies subthalamic low-frequency oscillations", Movement Disorders, vol. 32, No. 1, Nov. 8, 2016, pp. 80-88, doi: https://doi.org/10.1002/mds.26837.

Hebb et al., "Creating the feedback loop: Closed Loop Neurostimulation", Neurosurgery Clinics of North America, vol. 25, No. 1, Jan. 2014, pp. 187-204, DOI: 10.1016/j.NEC.2013.08.006.

Herron et al., "Bi-directional brain interfacing instrumentation", Proceedings of the IEEE International Instrumentation and Measurement Technology Conference (I2MTC), Houston, Texas, May 14-17, 2018, doi: 10.1109/I2MTC.2018.8409795.

Herron et al., "Embedding adaptive stimulation algorithms for a new implantable deep-brain stimulation research tool", Proceedings of the IEEE Biomedical Circuits and Systems Conference (BioCAS), Cleveland, Ohio, Oct. 17-19, 2018, doi: 10.1109/BIOCAS.2018.8584780.

Malekmohammadi et al., "Kinematic Adaptive Deep Brain Stimulation for Resting Tremor in Parkinson's Disease", Movement Disorders, vol. 31, No. 3, Jan. 27, 2016, pp. 426-428, doi: https://doi.org/10.1002/mds.26482.

Merola et al., "Parkinson's disease progression at 30 years: a study of subthalamic deep brain-stimulated patients", Brain, vol. 134, No. 7, Jul. 2011, pp. 2074-2084, doi: https://doi.org/10.1093/brain/awr121.

O'Day et al., "The turning and barrier course reveals gait parameters for detecting freezing of gait and measuring the efficacy of deep brain stimulation", bioRxiv, Jun. 14, 2019, 33 pgs, doi: https://doi.org/10.1101/671479.

Plotnik et al., "The role of gait rhythmicity and bilateral coordination of stepping in the pathophysiology of freezing of gait in Parkinson's disease", Movement Disorders, vol. 23, No. S2, Jul. 30, 2008, pp. S444-S450, doi: https://doi.org/10.1002/mds.21984.

Schlenstedt et al., "Effect of high-frequency subthalamic neurostimulation on gait and freezing of gait in Parkinson's disease: a systematic review and meta-analysis", European Journal of Neurology, vol. 24, No. 1, Oct. 20, 2016, pp. 18-26.

Stanslaski et al., "A Chronically Implantable Neural Coprocessor for Investigating the Treatment of Neurological Disorders", IEEE Transactions on Biomedical Circuits and Systems, vol. 12, No. 6, Dec. 2018, pp. 1230-1245, doi: 10.1109/TBCAS.2018.2880148.

Syrkin-Nikolau et al., "Subthalamic neural entropy is a feature of freezing of gait in freely moving people with Parkinson's disease", Neurobiology of Disease, vol. 108, Dec. 2017, pp. 288-297, doi: https://doi.org/10.1016/j.nbd.2017.09.002.

Velisar et al., "Dual threshold neural closed loop deep brain stimulation in Parkinson disease patients", Brain Stimulation, vol. 12, No. 4, Jul. 1, 2019, Electronic Publication: Feb. 25, 2019, pp. 868-876, doi: https://doi.org/10.1016/j.brs.2019.02.020.

* cited by examiner

SYSTEMS AND METHODS FOR DEEP BRAIN STIMULATION USING KINEMATIC FEEDBACK FOR TREATMENT OF MOVEMENT DISORDERS

CROSS REFERENCE TO RELATED APPLICATIONS

The present invention claims priority to U.S. Provisional Patent Application Ser. No. 63/144,432 entitled "Systems and Methods for Deep Brain Stimulation Kinematic Controllers" filed Feb. 1, 2021, the disclosure of which is herein incorporated by reference in its entirety for all purposes.

FIELD OF THE INVENTION

The present invention generally relates to using kinematic information about a patient to modify deep brain stimulation parameters to maintain therapeutic benefit.

BACKGROUND

Deep brain stimulation (DBS) is a neurosurgical treatment involving the placement of a neurostimulator (pulse generator) which sends electrical impulses through implanted electrodes to a specific target in the brain in order to treat a neurological condition. A common use of DBS is in the treatment of movement disorders. Movement disorders are a class of syndromes which have symptoms of involuntary excess or paucity of movement. Parkinson's disorder (PD) is a condition which often eventually requires DBS for management of symptoms.

PD is a long-term degenerative disorder of the central nervous system which strongly affects the motor system. The four cardinal signs of PD are tremor, slowness of movement (bradykinesia), rigidity, and postural instability. Freezing of gait (FoG) is another symptom of PD in which the patient is unable to move their feet forward despite intending to walk. FoG can cause serious falls as the freezing episode can occur suddenly while the person still has forward momentum. FoG is sometimes non-responsive to medication which can otherwise alleviate other PD symptoms.

Inertial measurement units (IMUs) are electronic devices which measure and report a body's specific force, angular rate, and sometimes the orientation of the body. Many IMUs are made of a 3-axis gyroscope and a 3-axis accelerometer.

SUMMARY OF THE INVENTION

Systems and methods for deep brain stimulation using kinematic feedback in accordance with embodiments of the invention are illustrated. One embodiment includes a deep brain stimulation system, including an implantable neurostimulator, a first inertial measurement unit (IMU), a second IMU, and a controller, where the controller is communicatively coupled to the implantable neurostimulator, the first IMU, and the second IMU, and where the controller is configured to obtain kinematic data from the first IMU and the second IMU, identify an abnormal movement event based on the kinematic data, and modify deep brain stimulation provided by the implantable neurostimulator based on the identified abnormal movement event.

In another embodiment, the first IMU is configured to be attached to the right leg of a patient; and the second IMU is configured to be attached to the left leg of the patient.

In a further embodiment, the kinematic data includes a signal of angular momentum over time.

In still another embodiment, the abnormal movement event is freezing of gait (FoG).

In a still further embodiment, in order to identify FoG, the controller is further configured to calculate metrics comprising: arrhythmicity over a most recent set of steps, stride time, swing angular range, and asymmetry over the most recent set of steps, and provide the calculated metrics to a logistic regression model to obtain a probability of an FoG event occurring.

In yet another embodiment, in order to modify the deep brain stimulation, the controller is further configured to determine a change in stimulation parameters using a stimulation map and the probability of an FoG event occurring.

In a yet further embodiment, the stimulation map includes the following changes in stimulation parameters: decrease stimulation intensity when the probability of an FoG event is below a minimum threshold, maintain stimulation intensity when the probability of an FoG event is between the minimum threshold and a maximum threshold and increase stimulation intensity when the probability of an FoG event is above the maximum threshold.

In another additional embodiment, the stimulation map includes the following changes in stimulation parameters: ramp stimulation frequency to 140 Hz when the probability of an FoG event is below a minimum threshold, maintain stimulation frequency when the probability of an FoG event is between the minimum threshold and a maximum threshold, and ramp stimulation frequency to 60 Hz when the probability of an FoG event is above the maximum threshold.

In a further additional embodiment, the minimum threshold is 30%, and the maximum threshold is 70%.

In another embodiment again, the abnormal movement event is arrhythmic gait identified by a coefficient of variation of stride times for a most recent set of previous steps exceeding a patient specific threshold.

In a further embodiment again, a method for deep brain stimulation includes obtaining kinematic data from a first IMU and a second IMU using a controller communicatively coupled to the first IMU and the second IMU, identifying an abnormal movement event based on the kinematic data using the controller, and modifying deep brain stimulation provided by an implantable neurostimulator communicatively coupled with the controller based on the identified abnormal movement event.

In still yet another embodiment, the first IMU is configured to be attached to the right leg of a patient; and the second IMU is configured to be attached to the left leg of the patient.

In a still yet further embodiment, the kinematic data includes a signal of angular momentum over time.

In still another additional embodiment, the abnormal movement event is freezing of gait (FoG).

In a still further additional embodiment, identifying FoG includes calculating metrics comprising: arrhythmicity over a most recent set of steps, stride time, swing angular range, and asymmetry over the most recent set of steps, and providing the calculated metrics to a logistic regression model to obtain a probability of an FoG event occurring.

In still another embodiment again, modifying the stimulation includes determining a change in stimulation parameters using a stimulation map and the probability of an FoG event occurring.

In a still further embodiment again, wherein the stimulation map includes the following changes in stimulation parameters: decrease stimulation intensity when the probability of an FoG event is below a minimum threshold, maintain stimulation intensity when the probability of an FoG event is between the minimum threshold and a maximum threshold, and increase stimulation intensity when the probability of an FoG event is above the maximum threshold.

In yet another additional embodiment, the stimulation map includes the following changes in stimulation parameters: ramp stimulation frequency to 140 Hz when the probability of an FoG event is below a minimum threshold, maintain stimulation frequency when the probability of an FoG event is between the minimum threshold and a maximum threshold, and ramp stimulation frequency to 60 Hz when the probability of an FoG event is above the maximum threshold.

In a yet further additional embodiment, the minimum threshold is 30%, and the maximum threshold is 70%.

In yet another embodiment again, the abnormal movement event is arrhythmic gait identified by a coefficient of variation of stride times for a most recent set of previous steps exceeding a patient specific threshold.

Additional embodiments and features are set forth in part in the description that follows, and in part will become apparent to those skilled in the art upon examination of the specification or may be learned by the practice of the invention. A further understanding of the nature and advantages of the present invention may be realized by reference to the remaining portions of the specification and the drawings, which forms a part of this disclosure.

BRIEF DESCRIPTION OF THE DRAWINGS

The description and claims will be more fully understood with reference to the following figures and data graphs, which are presented as exemplary embodiments of the invention and should not be construed as a complete recitation of the scope of the invention.

DETAILED DESCRIPTION

Figure 1:
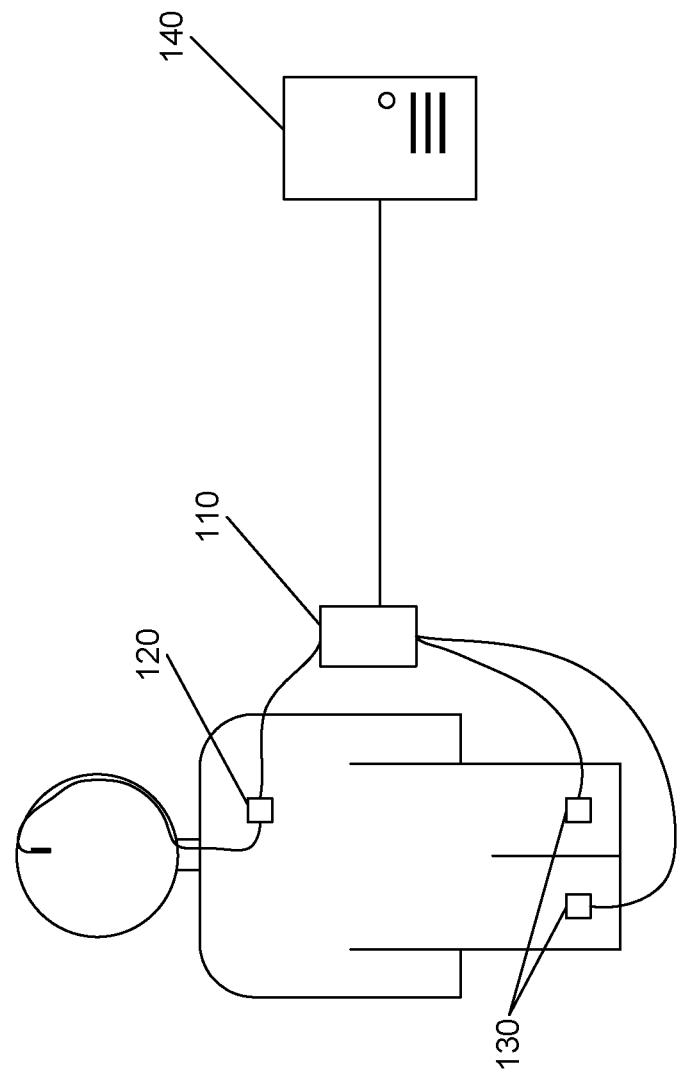
FIG. 1 is a diagram illustrating a DBS system in accordance with an embodiment of the invention.

Movement disorders tend to have severe and chronic impacts on the lives of patients who have them. While some movement symptoms can be treated with drugs, some conditions such as Parkinson's disorder (PD) tend to become drug-resistant after several years. When other interventions become unworkable, deep brain stimulation (DBS) becomes a more viable treatment option. DBS at 60 Hz or 140 Hz in PD patients has shown to be effective at treatment of freezing of gait (FoG) and gait arrhythmicity, although different frequencies may be more effective depending on the particular patient's brain.

Many DBS systems are "open-loop" which means that stimulation settings are manually input by a medical professional. DBS stimulation settings conventionally are clinically set by a medical professional during a process known as "programming." Some DBS systems enable different stimulation profiles to be optionally loaded by the medical professional that can be manually switched between by a patient between programming sessions. Some "closed-loop" DBS systems also exist which acquire biomarkers and can modify stimulation in response in order to have a more flexible system during real-time operation.

DBS systems described herein can use kinematic data obtained from sensors on a patient's body to recognize arrhythmicity of movement and/or FoG and modify DBS stimulation parameters in order to restore normal movement. In many embodiments, systems and methods described herein can predict symptomatic movement events such as (but not limited to) gait arrhythmicity and/or FoG and preemptively modify stimulation parameters in order to preclude the onset of the symptom. Inertial measurement units (IMUs) can be attached to the legs of a patient which can report back kinematic data describing the angular velocity of each limb. In various embodiments, kinematic data can include other information about the relative positions of each limb, and any other kinematic information about the limb the IMU is capable of collecting. Using the kinematic data, arrhythmicity and/or FoG can be identified, and stimulation parameters can be changed. Simulation parameters can include (but are not limited to) pulse frequency, pulse amplitude (i.e. intensity), and pulse train patterns. In some embodiments, the changes in stimulation parameters are made according to a stimulation map which indicates a change in one or more stimulation parameters in response to a likelihood of an abnormal movement event. DBS systems using kinematic feedback are discussed in further detail below.

DBS Systems Using Kinematic Feedback

DBS systems described herein can use one or more IMU's placed on a patient's body in order to capture kinematic data about a patient's movement and modify their stimulation parameters in near real time in order to respond to and alleviate abnormal movement conditions as they occur. In numerous embodiments, an IMU is placed on each leg of a patient. In various embodiments the IMU is placed on the shank, although said specific placement is not a requirement. The kinematic data recorded can be streamed to a controller which can detect and/or predict abnormal movement events and trigger a neurostimulator to modify the stimulation it is providing.

Turning now to FIG. 1, a DBS system using kinematic feedback in accordance with an embodiment of the invention is illustrated. Controller 110 is communicatively coupled to a neurostimulator 120 and two IMUs 130. In numerous embodiments, the controller communicates with the IMUs and the neurostimulator via one or more wireless connections. In various embodiments, the IMUs are externally worn devices, and the neurostimulator is an implanted device. The controller can be implemented using an external device or an internal device. In a variety of embodiments, the controller can be a smart phone, or other portable electronic device. The neurostimulator 120 provides electrical stimulation to a patient's brain via electrodes connected to the neurostimulator via one or more leads. In some embodiments, the controller and neurostimulator are integrated as a single implantable device.

Controller 110 also communicates with a programming device 140. In many embodiments, the programming device 140 is a computing device capable of providing updates to the controller. Updates can include new stimulation maps, new parameter settings, new predictive models, and/or any other type of update to the operation of the controller as needed. In various embodiments, the controller can provide data regarding its operation to the programming device for review by medical professionals. In many embodiments, controllers are capable of directly receiving programming via manual input without a programming device. Controllers and programming devices can be networked together. In many embodiments, the connection is wireless, although wired connections can be used instead or as well. Wireless connections can be made over networks such as (but not limited to) the Internet.

Figure 2:
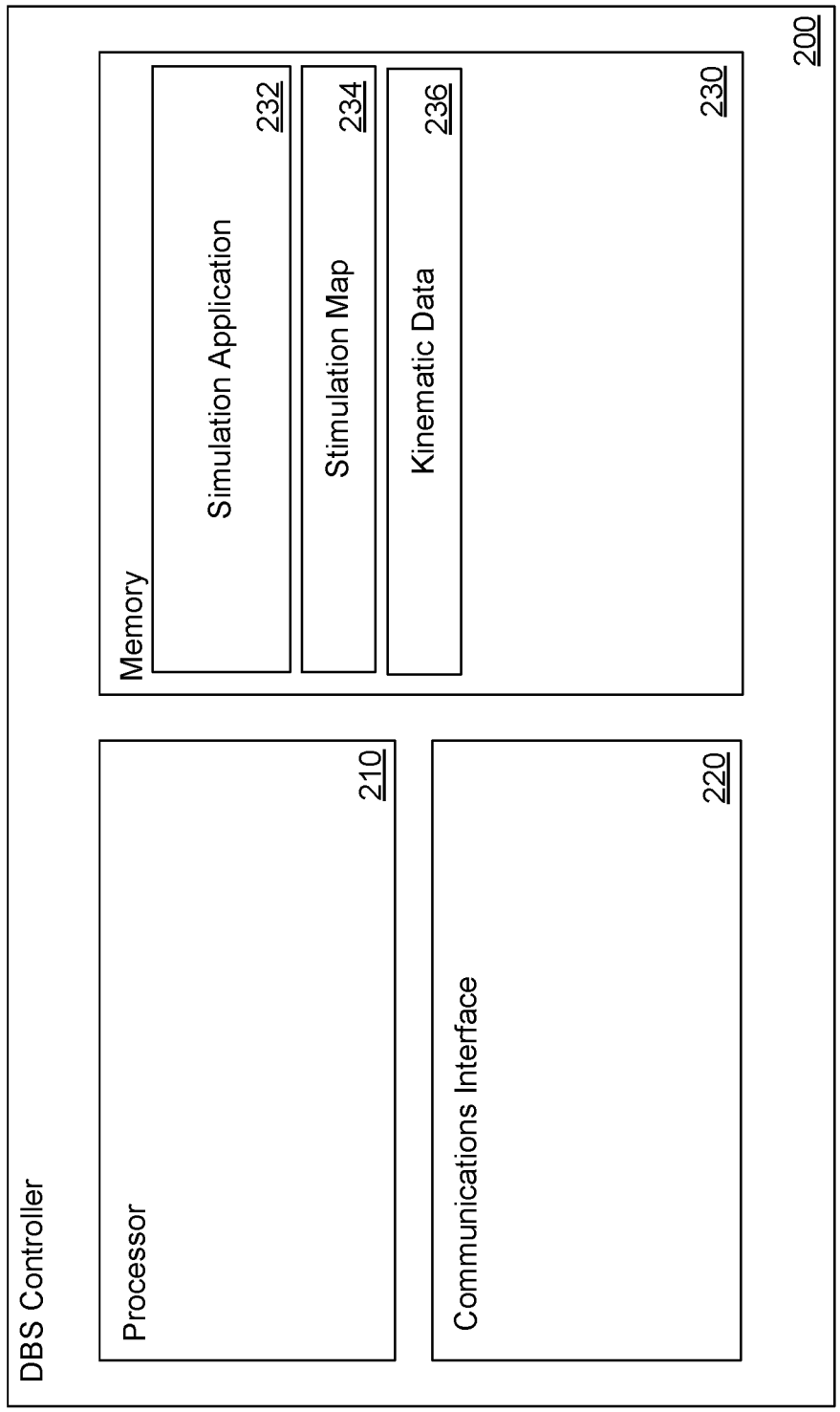
FIG. 2 is a block diagram for a DBS controller in accordance with an embodiment of the invention.

Turning now to FIG. 2, a block diagram for a controller in accordance with an embodiment of the invention is illustrated. DBS controller 200 includes a processor 210. Processor 210 can be any type of computational processing unit, including, but not limited to, microprocessors, central processing units, graphical processing units, parallel processing engines, or any other type of processor as appropriate to the requirements of specific applications of embodiments of the invention. Processors can include multiple processors and/or multiple types of processing architectures.

Controller 200 further includes a communications interface capable of communicating with IMUs, neurostimulators, programming devices, and/or any other device via appropriate communication methodologies as appropriate to the requirements of specific applications of embodiments of the invention. The controller 200 additionally includes a memory 230. The memory can be made of volatile and/or non-volatile memory. The memory 230 contains a stimulation application which is capable of directing the processor to generate stimulation parameters based on kinematic data received from IMU and provide said parameters to a neurostimulator. The memory 230 can also contain a stimulation map 234 which contains instructions on how to modify stimulation parameters in response to the probability of a detected abnormal movement event. In various embodiments, the memory 230 further contains kinematic data 236 obtained from IMUs.

While a specific system architecture and controller architecture are illustrated in FIGS. 1 and 2 respectively, as can readily be appreciated, any number of different architectures can be used as appropriate to the requirements of specific applications of embodiments of the invention. For example, different numbers of IMUs can be used and/or placed on different locations of the body. Processes for modifying stimulation parameters based on kinematic data are discussed in further detail below.

DBS Using Kinematic Feedback

Processes for modifying DBS parameters using kinematic feedback enable real-time closed-loop response to the changing condition of a patient. In many embodiments, FoG or arrhythmic gait is identified by processing kinematic data collected from IMUs attached to the patient's legs. In various embodiments, kinematic data contains angular momentum values over time for each leg. Individual steps can be identified within this time series of angular momentum as positive peaks in the signal. In many embodiments, the gait can be characterized using gait parameters such as (but not limited to) stride time, swing angular range, and swing time. Stride time is defined as the time period between two successive positive peaks in the angular velocity signal. Swing angular range is defined as the area under a peak in the angular velocity signal. Swing time is defined as the time between the initiation of the swing phase and the end of the swing phase for each step as determined from zero-crossings in the angular velocity signal.

From these metrics, gait arrhythmicity can be defined as the average coefficient of variation (CV) for the previous three stride times for left and right leg. Gait asymmetric can be defined as:100×|ln(SSWT/LSWT)|, where SSWT and LSWT correspond to the leg with the shortest and longest mean swing time, respectively. Further, probability of FoG can be detected using a logistic regression model. In many embodiments, the regression model uses four metrics: 1) arrhythmicity over the last six steps; 2) stride time; 3) swing angular range; and 4) asymmetry over the last six steps. By way of example, a model that accepts these metrics can take the form of:

$$P(FoG) = \frac{1}{1 + e^{-(0.941 + 2.034x_1 + 0.0931x_2 - 0.0615x_3 + 0.0003x_4)}}$$

where $x_1$, $x_2$, $x_3$, $x_4$, are the four metrics listed above, respectively. As can be readily appreciated, the coefficient values in the above equation are exemplary and have been experimentally determined and validated based on available data. One of ordinary skill in the art can appreciate that the specific values of the coefficients can be varied for a particular patient based on available records without departing from the scope or spirit of the invention, and that the specific values listed are non-limiting.

In numerous embodiments, gait arrhythmicity can be used as a surrogate for FoG. For example, in some embodiments, steps that are identified as arrhythmic to a degree above a patient-specific threshold can be classified as FoG as a backstop against improper detection. The patient-specific threshold can be determined from analysis of the patient's gait and a determination by a medical professional.

Further, in many embodiments, a machine learning model can be used instead of a regression which classifies steps as FoG. In numerous embodiments, the machine learning model can be trained on a training data set comprising annotated kinematic data. In various embodiments, the machine learning model can be further trained on patient-specific annotated training data to have a more personalized model.

Figure 3:
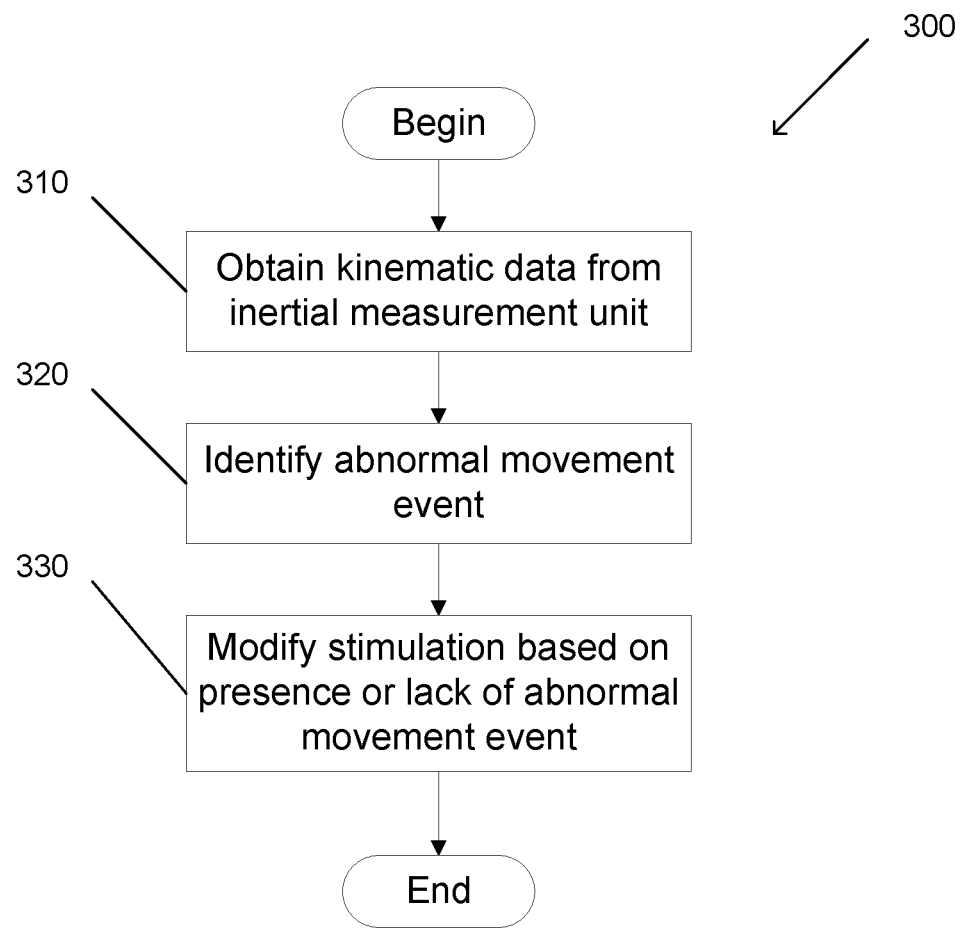
FIG. 3 is a flow chart illustrating a method for DBS using kinematic feedback in accordance with an embodiment of the invention.

Turning now to FIG. 3, a process for modifying stimulation parameters based on kinematic data in accordance with an embodiment of the invention is illustrated. Process 300 includes obtaining (310) kinematic data from one or more IMU's attached to the patient. As noted above, in numerous embodiments, the IMUs are attached to the legs of the patient. Abnormal movement events are identified (320) in the kinematic data. In various embodiments, the abnormal movement event is FoG. In many embodiments, the abnormal movement event is arrhythmic gait. Depending on whether or not an abnormal movement event is identified, the stimulation parameters can be modified. In numerous embodiments, a stimulation map is used to guide the modification.

For example, at each timestep i, the probability of FoG at timestep i, P(i) is used to determine how to modify the stimulation parameters. In the following, $P_{min}$ is the normal step probability threshold, and $P_{max}$ is the freezing step probability threshold. If $P(i) < P_{min}$, then the stimulation intensity can be reduced and/or the frequency can be ramped to 140 Hz. If $P_{min} < P(i) < P_{max}$, then no modification to the stimulation parameters is made. If $P_{max} < P(i)$, then stimulation intensity can be increased and/or the frequency can be ramped to 60 Hz. In various embodiments, $P_{min}$=30%, and $P_{max}$=70%. However, these can each be varied by +/−10% depending on the particular patient. With respect to ramping intensity, further rules can be established in order to maintain intensity within safe bounds.

Figure 4:
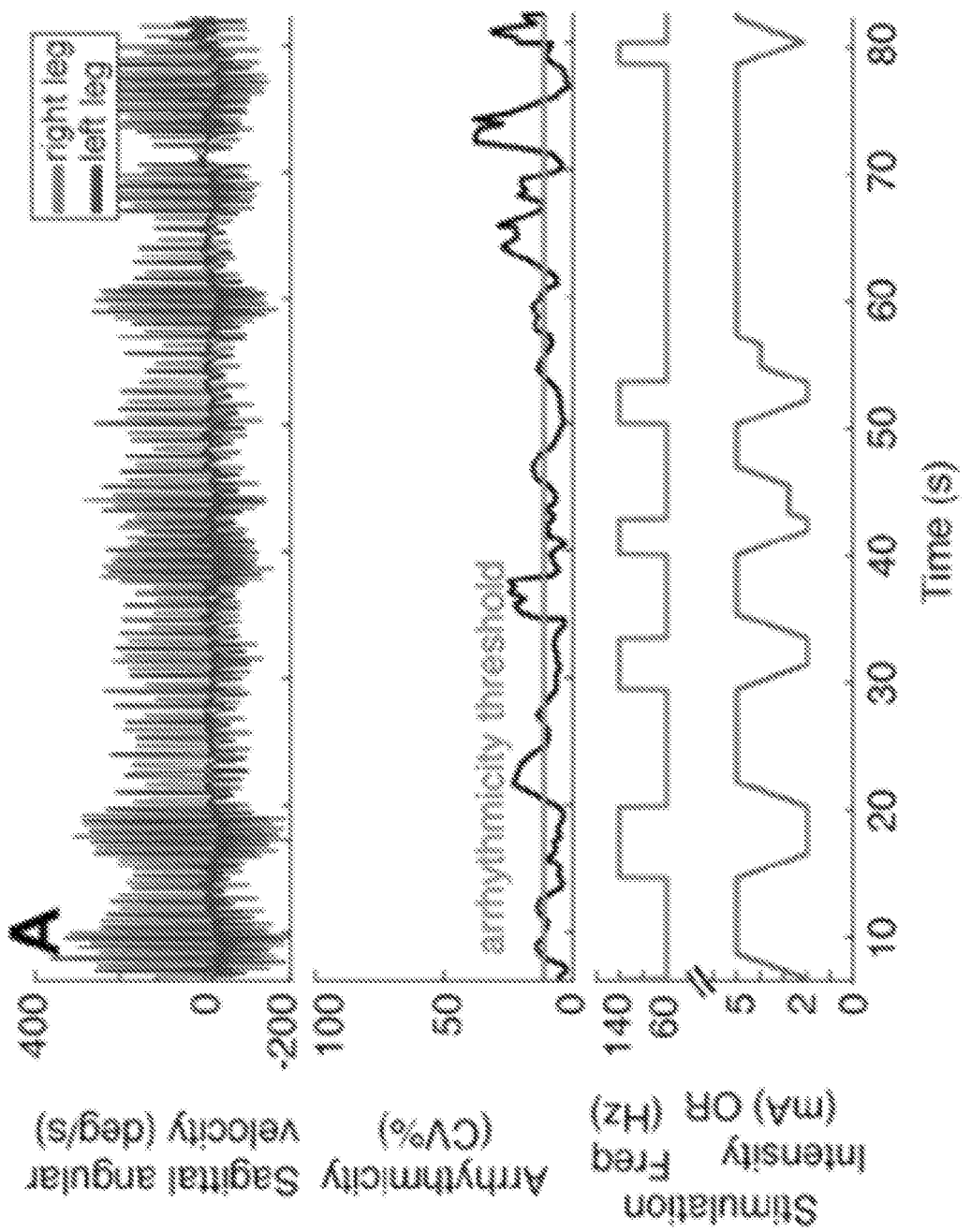
FIG. 4 is a chart showing changes in example stimulation in response to detected levels of arrhythmicity in accordance with an embodiment of the invention.
Figure 5:
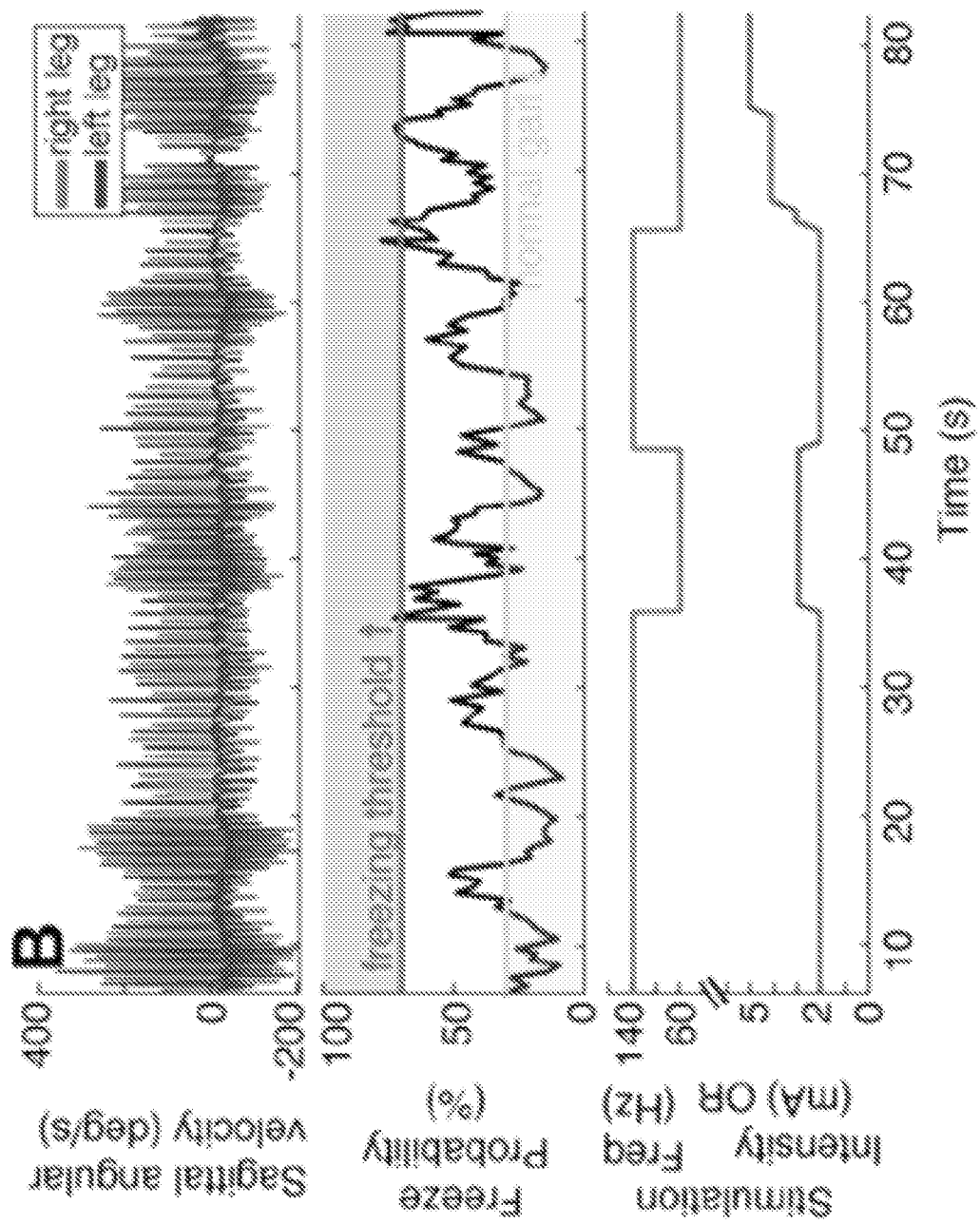
FIG. 5 is a chart showing changes in example stimulation in response to likelihood of FoG in accordance with an embodiment of the invention.

As can be readily appreciated, the specific frequencies have been determined experimentally to be therapeutic, however different frequencies may be more appropriate for a particular patient's brain, and therefore these numbers may be modified without departing from the scope or spirit of the invention. Turning now to FIG. 4, a set of charts illustrating example angular velocity signals, coefficients of variation, and stimulation intensity/frequency changes based on an arrhythmicity threshold used as a surrogate for FoG in accordance with an embodiment of the invention are illustrated, respectively. FIG. 5 illustrates a set of charts based on the same example angular velocity signals, but instead showing the calculated freeze probability over time and resulting changes in stimulation intensity/frequency based on said probability in accordance with an embodiment of the invention. Using systems and methods described herein, patient's FoG symptoms can be ameliorated in real time.

Although specific systems and methods for DBS using kinematic feedback are discussed above, many different systems and methods can be implemented in accordance with many different embodiments of the invention. It is therefore to be understood that the present invention may be practiced in ways other than specifically described, without departing from the scope and spirit of the present invention. Thus, embodiments of the present invention should be considered in all respects as illustrative and not restrictive. Accordingly, the scope of the invention should be determined not by the embodiments illustrated, but by the appended claims and their equivalents.

What is claimed is:

1. A deep brain stimulation system, comprising:
   an implantable neurostimulator;
   a first inertial measurement unit (IMU);
   a second IMU; and
   a controller, where the controller is communicatively coupled to the implantable neurostimulator, the first IMU, and the second IMU, and where the controller is configured to
   obtain kinematic data from the first IMU and the second IMU;
   predict a likelihood of a freezing of gait (FoG) event based on the kinematic data; and
   modify deep brain stimulation provided by the implantable neurostimulator based on the predicted likelihood, wherein the modification comprises:
      decreasing stimulation intensity when the predicted likelihood is below a minimum threshold;
      maintaining stimulation intensity when the predicted likelihood is between the minimum threshold and a maximum threshold; and
      increasing stimulation intensity when the predicted likelihood is above the maximum threshold.

2. The deep brain stimulation system of claim 1, wherein the first IMU is configured to be attached to the right leg of a patient; and the second IMU is configured to be attached to the left leg of the patient.

3. The deep brain stimulation system of claim 1, wherein the kinematic data comprises a signal of angular momentum over time.

4. The deep brain stimulation system of claim 1, wherein in order to predict a likelihood of the FoG event, the controller is further configured to:
   calculate metrics comprising: arrhythmicity over a most recent set of steps, stride time, swing angular range, and asymmetry over the most recent set of steps; and
   provide the calculated metrics to a logistic regression model to obtain a probability of the FOG event occurring.

5. The deep brain stimulation system of claim 1, further comprising modifying the deep brain stimulation according to a stimulation map, wherein the stimulation the stimulation map comprises the following changes in stimulation parameters:
   ramp stimulation frequency to 140 Hz when the predicted likelihood is below a minimum threshold;
   maintain stimulation frequency when the predicted likelihood is between the minimum threshold and a maximum threshold; and
   ramp stimulation frequency to 60 Hz when the predicted likelihood is above the maximum threshold.

6. The deep brain stimulation system of claim 5, wherein the minimum threshold is 30%, and the maximum threshold is 70%.

7. A method for deep brain stimulation, comprising:
   obtaining kinematic data from a first inertial measurement unit (IMU) and a second IMU using a controller communicatively coupled to the first IMU and the second IMU;
   predict a likelihood of a freezing of gait (FoG) event based on the kinematic data using the controller; and
   modifying deep brain stimulation provided by an implantable neurostimulator communicatively coupled with the controller based on the predicted likelihood, wherein the modification comprises:
      decreasing stimulation intensity when the predicted likelihood is below a minimum threshold;
      maintaining stimulation intensity when the predicted likelihood is between the minimum threshold and a maximum threshold; and
      increasing stimulation intensity when the predicted likelihood is above the maximum threshold.

8. The method of deep brain stimulation of claim 7, wherein the first IMU is configured to be attached to the right leg of a patient; and the second IMU is configured to be attached to the left leg of the patient.

9. The method of deep brain stimulation of claim 7, wherein the kinematic data comprises a signal of angular momentum over time.

10. The method of deep brain stimulation of claim 7, wherein predicting the likelihood of the FoG event comprises:
    calculating metrics comprising: arrhythmicity over a most recent set of steps, stride time, swing angular range, and asymmetry over the most recent set of steps; and
    providing the calculated metrics to a logistic regression model to obtain a probability of the FOG event occurring.

11. The method of deep brain stimulation of claim 7, further comprising modifying the deep brain stimulation according to a stimulation map, wherein the stimulation map comprises the following changes in stimulation parameters:
    ramp stimulation frequency to 140 Hz when the predicted likelihood is below a minimum threshold;
    maintain stimulation frequency when the predicted likelihood is between the minimum threshold and a maximum threshold; and
    ramp stimulation frequency to 60 Hz when the predicted likelihood is above the maximum threshold.

12. The method of deep brain stimulation of claim 11, wherein the minimum threshold is 30%, and the maximum threshold is 70%.

\* \* \* \* \*

UNITED STATES PATENT AND TRADEMARK OFFICE
CERTIFICATE OF CORRECTION

| | | |
|---|---|---|
| PATENT NO. | : 12,109,417 B2 | Page 1 of 1 |
| APPLICATION NO. | : 17/649667 | |
| DATED | : October 8, 2024 | |
| INVENTOR(S) | : Helen Bronte-Stewart et al. | |

It is certified that error appears in the above-identified patent and that said Letters Patent is hereby corrected as shown below:

In the Specification

Column 1, Line 5: Please insert
--STATEMENT OF FEDERALLY SPONSORED RESEARCH
This invention was made with Government support under contract NS107709 awarded by the National Institutes of Health. The Government has certain rights in the invention.--.

Signed and Sealed this
Eighth Day of April, 2025

Coke Morgan Stewart
*Acting Director of the United States Patent and Trademark Office*